United States Patent [19]

Park et al.

[11] Patent Number: 5,175,331
[45] Date of Patent: Dec. 29, 1992

[54] PROCESS FOR PREPARATION OF ORGANOSILICON HALIDES

[75] Inventors: Won S. Park; William R. Beard, both of Baton Rouge, La.

[73] Assignee: Ethyl Corporation, Richmond, Va.

[21] Appl. No.: 809,430

[22] Filed: Dec. 18, 1991

[51] Int. Cl.$^5$ .............................. C07F 7/08; C07F 7/12
[52] U.S. Cl. .................................................. 556/478
[58] Field of Search ......................................... 556/478

[56] References Cited

U.S. PATENT DOCUMENTS

| | | | |
|---|---|---|---|
| 2,762,824 | 9/1956 | Brown | 556/478 |
| 3,927,058 | 12/1975 | Libbey | 556/478 |
| 3,927,059 | 12/1975 | Libbey et al. | 556/478 |
| 3,927,060 | 12/1975 | Libbey | 556/478 |
| 4,155,927 | 5/1979 | Straussberger et al. | 556/478 |
| 4,946,980 | 8/1990 | Halm et al. | 556/478 |

*Primary Examiner*—Paul F. Shaver
*Attorney, Agent, or Firm*—Richard J. Hammond

[57] ABSTRACT

A process for preparing a silane mixture of the formula $$Si\,R_nX_{4-n}$$

where R is $C_1$ to $C_{12}$ linear or branched alkyl, phenyl or phenyl substituted with one or more $C_1$ to $C_6$ linear or branched alkyl; X is chloro, bromo or iodo; and n is an integer from 1 to 4; comprising reacting silicon tetrafluoride with metallic aluminum and RX, where R and X are as previously described, at a temperature of about 150° C. to about 400° C.

5 Claims, No Drawings

PROCESS FOR PREPARATION OF ORGANOSILICON HALIDES

This invention relates to the manufacture of silicon compounds and more particularly to a new process for making organosilicon halides.

Organosilicon halides, as for example, methylsilicon chlorides ($MeSiCl_3$, $Me_2SiCl_2$, $Me_3SiCl$), are manufactured commercially by reacting methylchloride with elemental silicon or by reacting Grignard reagents with silicon halide compounds. These processes have several disadvantages particularly with regard to the economics of the use of catalysts and reagents.

U.S. Pat. No. 2,762,824 discloses the manufacture of organosilicon halides such as the alkyl and aryl silicon halides directly from the corresponding alkyl- and arylaluminum halides by reaction with silicon tetrafluoride. These alkyl- and arylaluminum halides can be prepared by means from alkyl or aryl halides and aluminum metal.

The reaction disadvantageously proceeds in two steps and requires the isolation of an intermediate mixture of alkyl or aryl aluminum halides which are in turn further reacted with silicon tetrafluoride at significantly higher temperatures. The final product is an essentially equal mixture of $(CH_3)_3SiCl$, $(CH_3)_2SiCl_2$, and $CH_3SiCl_3$ when methyl chloride is employed.

It is accordingly an object of this invention to provide an improved process for preparing compounds of the above type in a single reaction step. Other objects and advantages of this invention will become apparent as the description proceeds.

A wide variety of organosilicon halides can be manufactured according to this invention. Typical examples of alkyl substitutions are methyl, ethyl, propyl, isopropyl, normal butyl, isobutyl and heptyl.

The process according to the present invention utilizes a mixture of metallic aluminum with silicon tetrafluoride and an alkyl or aryl halide.

Normally, the halides which are most useful in this invention are confined to the chlorides, bromides and iodides. Although slight reaction is obtained with some fluorides, they are of generally less importance.

Typical examples of alkyl and aryl halides suitable for reaction with aluminum are methyl chloride, ethyl chloride, isopropyl chloride, n-propyl chloride, ethyl bromide, methyl bromide, methyl iodide, ethyl iodide, n-propyl iodide, isopropyl iodide, hexyl iodide, heptyl iodide, octyl iodide, p-tolyl iodide and phenyl iodide.

Each of the above alkyl and aryl halides results in corresponding alkyl or aryl silicon halides. For example, when methyl chloride is employed, the final product is $(CH_3)_2SiCl_2$ mixed with $(CH_3)_3SiCl$, $CH_3SiCl_3$ and other methylsilicon compounds. Likewise, when ethyl chloride or methyl bromide is employed, the final products are $(C_2H_5)_2SiCl_2$ and $(CH_3)_2SiBr_2$, respectively.

Other typical examples of organosilicon halides which can be made by this invention are as follows: diphenyl silicon iodide, phenyl silicon iodide, naphthyl silicon bromide, naphthyl silicon iodide and benzyl silicon chloride.

The reaction is preferably carried out in the presence of a Lewis acid catalyst, such as methylaluminum sesquichloride, aluminum chloride or iodine. In general, it is desired to use between about 0.05-0.2% of catalyst based upon the weight of the aluminum.

A more preferred range of catalyst is 0.075-0.15%. Higher concentrations can be used, but such concentrations do not materially increase the reaction rate and also tend to contaminate the product. In some cases, lower concentrations can be employed.

The reaction is generally carried out at a pressure of between about 1 and 20 atmospheres. Normally, it is preferred to maintain the pressure between about 1 and 5 atmospheres. The reaction temperature should be maintained above 150° C. to about 400° C., because the reaction rate is materially reduced at lower temperatures. A preferred temperature of operation is between 50°-350° C. This reaction is normally carried out in the absence of any solvent, since in many instances the catalyst tends to form a complex with the solvent.

A wide variety of concentrations of reactants can be employed in this reaction. However, stoichiometric quantities are generally preferred. Also, it is normally preferred to use the aluminum in the form of powder, chips, granules or other subdivided form.

The reaction can be carried out in a wide variety of reaction vessels. A glass-lined stirred autoclave is ordinarily preferred. However, in a continuous operation, a tube type reactor can be employed.

The following examples are working examples and are for illustrative purposes only.

All reactions and handling of air-sensitive materials were conducted in a nitrogen atmosphere; GC/MS analyses were performed using a Finnegan 4500 Gas Chromatograph/Mass Spectrometer. The aluminum, silicon and titanium levels were determined by ICP spectroscopy using a Perkins-Elmer Plasma II emission spectrometer. Products were identified by comparing analytical results with those of authentic commercial samples. MASC is methylaluminum sesquichloride.

| | REACTIONS OF ALUMINUM POWDER WITH MeCl and $SiF_4$[a] | | | | | | | |
|---|---|---|---|---|---|---|---|---|
| EXAMPLE | Al/g | MeCl/ mmHg[b] | $SiF_4$/ mmHg[b] | Ti in Al/% | Time/h | Additive/g | Temp/°C. | $SiF_4$ recovered | $Me_nSiCl_{4-n}$ Yield %[c] |
| 1 | 2.16 | 6.3 g | 6.3 g | 2.14 | 2 | MASC, 0.21 | 350 | 28.7% of chgd | 79(32)[c] |
| 2 | 0.54 | 612 | 612 | 2.14 | 3 | MASC, 0.21 | 200 | 20.% of chgd | 76.0(2)[c] |
| 3 | 2.16 | 1,223 | 612 | 2.14 | 3 | MASC, 0.21 | 200 | 21.5% of chgd | 72.6 |
| | | 1,257 | 615 | | | | | | 90.6[d] |
| | | 1,293 | 609 | | | | | | |
| | | 1,308 | 657 | | | | | | |
| | | 1,318 | 640 | | | | | | |
| | | 1,010 | 500 | | | | | | |
| | | 7,409 | 3,633 | | | | | | |
| 4 | 2.16 | 1,247 | 669 | 0.19 | 3 | MASC, 0.21 | 200 | — | 56 |
| 5 | 2.16 | 1,300 | 610 | 0.19 | 3 | — | 200 | 100% | 0 |

| | | REACTIONS OF ALUMINUM POWDER WITH MeCl and SiF₄ᵃ | | | | | | | |
|---|---|---|---|---|---|---|---|---|---|
| EXAMPLE | Al/g | MeCl/ mmHgᵇ | SiF₄/ mmHgᵇ | Ti in Al/% | Time/h | Additive/g | Temp/°C. | SiF₄ recovered % of chgd | MeₙSiCl₄₋ₙ Yield %ᶜ |

ᵃExamples 2–5, 110–150 psig max. pressure. Example 1, 250 psig.
ᵇKnown amounts of gases were transferred using a precalibrated bulb of about 300 cc volume. The bulb was attached to a manifold equipped with an Hg manometer.
ᶜYields were calculated by assuming that all of the liquid products were dimethyldichlorosilane.
ᵈBased on SiF₄ consumed.
ᵉNumbers in parentheses are relative % of dichlorodimethylsilane.

We claim:

1. A process for preparing a silane mixture of the formula $$SiR_nX_{4-n}$$

where R is $C_1$ to $C_{12}$ linear or branched alkyl, phenyl or phenyl substituted with one or more $C_1$ to $C_6$ linear or branched alkyl; X is chloro, bromo or iodo; and n is an integer from 1 to 4; which comprises reacting silicon tetrafluoride with RX, where R and X are as previously described, and metallic aluminum at a temperature of about 150° C. to about 400° C.

2. The process according to claim 1 wherein said temperature is from about 150° C. to about 350° C.

3. The process according to claim 2 wherein R is $C_1$ to $C_6$ linear or branched alkyl and X is chloro.

4. The process according to claim 3 wherein R is methyl.

5. The process according to claim 4 wherein n is 2.

* * * * *